United States Patent [19]

Welch, Jr.

[11] 4,044,137

[45] Aug. 23, 1977

[54] 2-(PHENYLTHIOPROPYL)-5-ARYL-1,2,3,4-TETRAHYDRO-γ-CARBOLINES

[75] Inventor: Willard M. Welch, Jr., Mystic, Conn.

[73] Assignee: Pfizer Inc., New York, N.Y.

[21] Appl. No.: 703,175

[22] Filed: July 7, 1976

[51] Int. Cl.$^2$ .................. A61K 31/44; C07D 471/04
[52] U.S. Cl. ..................... 424/256; 260/294.8 B; 260/296 A
[58] Field of Search ............ 260/294.8 B, 296 A; 424/256

[56] References Cited

U.S. PATENT DOCUMENTS

| 3,654,289 | 4/1972 | Paris et al. | 260/295 C |
| 4,001,263 | 1/1977 | Plattner et al. | 260/296 A |

Primary Examiner—Alan L. Rotman
Attorney, Agent, or Firm—Connolly and Hutz

[57] ABSTRACT

2-(Phenylthiopropyl)-5-aryl-1,2,3,4-tetrahydro-γ-carboline tranquilizing agents and the preparation thereof from 5-aryl-1,2,3,4-tetrahydro-γ-carbolines.

11 Claims, No Drawings

2-(PHENYLTHIOPROPYL)-5-ARYL-1,2,3,4-TETRAHYDRO-γ-CARBOLINES

BACKGROUND OF THE INVENTION

Following the introduction of reserpine and chlorpromazine into psychotherapeutic medicine in the early 1950's, great effort has been expended in the search for other tranquilizing agents having improved biological profiles.

It has now been found that certain indoles, and more particularly, a series of 2-phenylthio- and 2-phenylsulfinylpropyl-5-aryl-1,2,3,4-tetrahydro-γ-carboline derivatives, are effective as tranquilizing agents.

γ-Carbolines are not new in the chemical and patent literature; antihistamine activity is reported in British patent 721,171 and U.S. Pat. Nos. 2,786,059 and 3,409,628; antidepressant activity in U.S. Pat. Nos. 3,419,568, 3,687,960, 3,705,902 and 3,718,657; antitrypanosomal activity in U.S. Pat. No. 3,654,289 and German Pat. Nos. 2,117,286 and 2,115,738; depressant and analgesic activity in U.S. Pat. Nos. 3,466,293, 3,502,688 and 3,382,250; and tranquilizing activity in U.S. Pat. Nos. 3,687,961 and 3,755,584.

Belgium Pat. Nos. 827,451 claims a series of γ-carbolines and pyrrolo[3,4-b]indoles as tranquilizing agents.

None of these aforementioned references suggest the compounds of the present invention or the use thereof as tranquilizing agents.

SUMMARY OF THE INVENTION

The tranquilizing agents of this invention are represented by the formula:

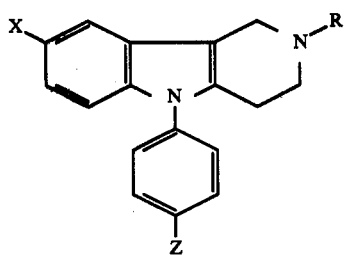

and the pharmaceutically acceptable acid addition salts thereof, wherein X is fluoro, chloro, bromo or hydrogen; Z is hydrogen, fluoro, chloro or methoxy; and R is

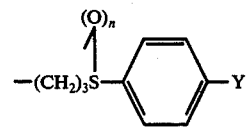

wherein $n$ is an integer of 0 or 1 and Y is fluoro, chloro, methyl or hydrogen.

A preferred group of compounds are those wherein $n$ is 0 and Y is fluoro. Especially preferred within this group are those tranquilizing agents wherein X and Z are each fluoro, wherein X is chloro and Z is fluoro and wherein X is fluoro and Z is hydrogen.

A second preferred group of compounds are those wherein $n$ is 1 and Y is fluoro. Especially preferred within this second group are those compounds wherein X and Z are each fluoro, wherein X is chloro and Z is fluoro and wherein X is fluoro and Z is hydrogen.

DETAILED DESCRIPTION OF THE INVENTION

In accordance with the process employed for synthesizing the compounds of the present invention, the following scheme is illustrative:

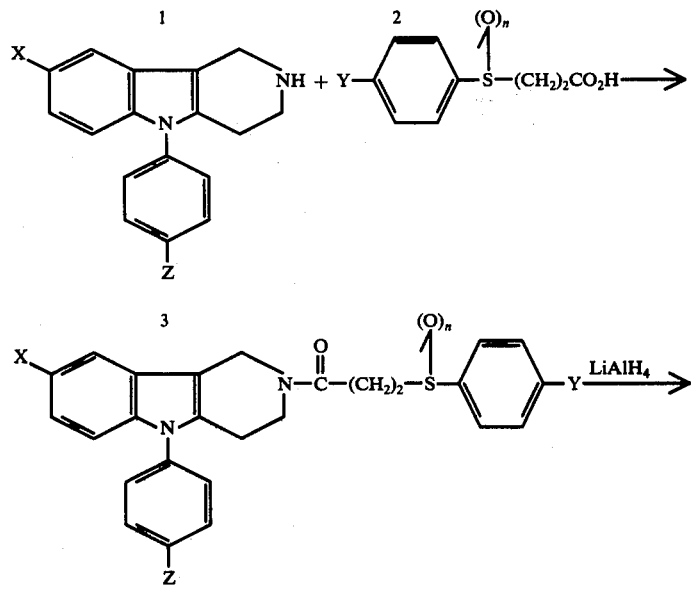

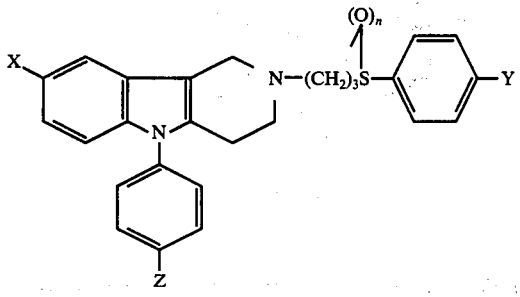

wherein X, Y, Z and n are as previously defined.

In practice, the γ-carbolines 1 are coupled with the appropriate phenylthiopropionic acid in a reaction-inert-solvent in the presence of a carbodiimide at temperatures of 0°–5° C.

The most suitable solvents for this reaction are those which solubilize the reactants to at least a moderate amount, and do not react appreciably with either the reactants or the products formed. In this coupling reaction such solvents as methylene chloride, chloroform, benzene, dimethylformamide and tetrahydrofuran are operable; the preferred solvent is methylene chloride.

It is preferred that the active acylating agent be prepared by combining equimolar amounts of the appropriate phenylthiopropionic acid and a carbodiimide, such as dicyclohexylcarbodiimide, followed by the addition of the appropriate γ-carboline 1. The active O-acyl urea resulting from a combination of the carbodiimide and acid 2 is best prepared at ice-bath temperature, a reaction time of 15–30 minutes being required.

When the activated acid is prepared, the γ-carboline 1, in equimolar amounts, is added in one of the suitable reaction-inert-solvents. The ice-bath cooling preferred for the formation of the activated acid should also be maintained for the coupling step with 1. The reaction is then allowed to warm to room temperature where it is allowed to stir overnight.

Reaction times are not critical, and are dependent on concentration, inherent reactivity and temperature. The cooling portion of the coupling reaction requires about 2–3 hours and is virtually complete by that time. Allowing the reaction to warm to room temperature insures completion.

The urea by-product is filtered and the solvent removed in vacuo. The residual product 3 can be purified by recrystallization from an appropriate solvent, or some other method of refinement.

Reduction of 3 to give the products of the present invention is effected with lithium aluminum hydride in a reaction-inert-solvent.

By such solvents is meant those in which the reactants have some solubility and which do not react to any extent with either the reactants or products. Especially preferred is tetrahydrofuran.

The order of addition is not wholly critical to the outcome of the reaction. Convenience and results suggest that the hydride in solution be added to a solution of the amide 3. In theory one mole of the amide is reduced to the desired product with one-half mole of the hydride. In practice, it is preferred, to insure completeness of reaction, to use an excess of the hydride; said excess can be 50–100% without altering the course of the reaction.

Reaction temperatures are not critical. It is preferred that a solution of the hydride be added to a gently refluxing solution of 3. Generally the reaction is complete when the addition is complete. Further heating at reflux for 30–45 minutes ensures completeness of reaction.

At the completion of the reaction, water is cautiously added to hydrolyze the cooled reaction mixture. The precipitate is filtered and product extracted with ethyl acetate. The removal of the solvent leaves the crude product, which can be subsequently further purified by recrystallization of the free base or an appropriate acid addition salt.

The requisite starting reagents of formula 1 are compounds known in the art, and are prepared according to the procedures in Belgium Pat. No. 827,451.

The appropriate phenylthiopropionic (n=0) acids are prepared by alkylation of the corresponding thiophenol with β-bromopropionic acid. Oxidation of the phenylthiopropionic acid with sodium periodate provides those intermediates wherein n=1.

As has been previously mentioned, the compounds of the present invention can form acid addition salts. Said basic compounds are converted to their acid addition salts by interaction of the base with an acid either in an aqueous or nonaqueous medium. In a similar manner, treatment of the acid addition salts with an equivalent amount of an aqueous base solution, e.g., alkali metal hydroxides, alkali metal carbonates and alkali metal bicarbonates or with an equivalent amount of a metal cation which forms an insoluble precipitate with the acid anion, results in the regeneration of the free base form. The bases thus regenerated may be reconverted to the same or a different acid addition salt.

In the utilization of the chemotherapeutic activity of those compounds of the present invention, it is preferred, of course, to use pharmaceutically acceptable salts. Although water-insolubility, high toxicity, or lack of crystalline nature may make some particular salt species unsuitable or less desirable for use as such in a given pharmaceutical application, the water insoluble or toxic salts can be converted to the corresponding pharmaceutically acceptable bases by decomposition of the salt as described above, or alternately, they can be converted to any desired pharmaceutically acceptable acid addition salt.

Examples of acids which provide pharmaceutically acceptable anions are hydrochloric, hydrobromic, hydroiodic, nitric, sulfuric, or sulfurous, phophoric, acetic, lactic, citric, tartaric, succinic, maleic and gluconic acids.

As previously indicated, the γ-carbolines of the present invention are readily adapted to therapeutic use as tranquilizing agents in mammals. Outstanding for their effectiveness in these regards are the following agents:
8-fluoro-5-(p-fluorophenyl)-2-[3-(p-fluorophenylthio)propyl]-1,2,3,4-tetrahydro-γ-carboline; 8-chloro-5-(p- fluorophenyl)-2-[3-(p-fluorophenylthio]-propyl]-propyl]-1,2,3,4-tetrahydro-γ-carboline; 8-fluoro-5-phenyl-2-[3-(p-fluorophenylthio)propyl]-1,2,3,4-tetrahydro-γ-carboline; 8-fluoro-5-(p-fluorophenyl)-2-[3-(p-fluorophenylsulfinyl)propyl]-1,2,3,4-tetrahydro-γ-carboline; 8-chloro-5-(p-fluorophenyl)-2-[3-(p-fluorophenylsulfinyl)propyl]-1,2,3,4-tetrahydro-γ-carboline; and 8-fluoro-5-phenyl-2-(3-[p-fluorophenylsulfinyl)-propyl]-1,2,3,4-tetrahydro-γ-carboline.

The tranquilizing agents of the present invention are characterized by relief of such schizophrenic manifestations in humans as hallucinations, hostility, suspiciousness, emotional or social withdrawal, anxiety, agitation and tension. Standard procedures of detecting and comparing tranquilizing activity of compounds in this series and for which there is an excellent correlation with human efficacy is the antagonism of amphetamine-induced symptoms in rats test, as taught by A. Weissman, et al., *J. Pharmacol. Exp. Ther.*, 151, 339 (1966) and by Quinton, et al., *Nature*, 200, 178 (1963).

The γ-carbolines and the pharmaceutically acceptable salts thereof, which are useful as tranquilizers, can be administered either as individual therapeutic agents or as mixtures of therapeutic agents. They may be administered alone,, but are generally administered with a pharmaceutical carrier selected on the basis of the chosen route of administration and standard pharmaceutical practice. For example, they can be administered orally in the form of tablets or capsules containing such excipients as starch, milk sugar, or certain types of clay, etc. They can be administered in the form of elixirs or oral suspensions with the active ingredients combined with emulsifying and/or suspending agents. They may be injected parenterally, and for this use they, or appropriate derivatives, may be prepared in the form of sterile aqueous solutions. Such aqueous solutions should be suitably buffered, if necessary, and should contain other solutes such as saline or glucose to render them isotonic.

Although the use of the present invention is directed toward the treatment of mammals in general, the preferred subject is humans. In determining an efficacious dose for human therapy, results of animal testing are frequently extrapolated and a correlation is assumed between animal test behavior and proposed human dosage. When a commercially employed standard is available, the dose level of the clinical candidate in humans is frequently determined by comparison of its performance with the standard in an animal test. For example, if a standard tranquilizing agent is administered effectively to humans at the rate of 100 to 400 mg. daily, it is assumed, then, that if compounds of the present invention have activity comparable to this standard in the test assay, that similar doses will provide comparable responses in humans.

Obviously, the physician will ultimately determine the dosage which will be most suitable for a particular individual, and it will vary with age, weight and response of the particular patient, as well as with the nature and extent of the symptoms and the pharmacodynamic characteristics of the particular agent to be administered. Generally, small doses will be administered initially, with a gradual increase in the dosage until the optimum level is determined. It will often be found that when the composition is administered orally, larger quantities of the active ingredient will be required to produce the same level as produced by a smaller quantity administered parenterally.

Having full regard for the foregoing factors, it is considered that a daily dosage of the compounds of the instant invention in humans of approximately 10 to 500 mg., with a preferred range of 10 to 250 mg., will tranqilize effectively. These values are illustrative, and there may, of course, be individual cases where higher or lower dose ranges are merited.

The following examples are provided solely for the purpose of illustration and are not to be construed as limitations of this invention, many variations of which are possible without departing from the spirit or scope thereof.

EXAMPLE 1

8-Fluoro-5-(p-fluorophenyl)-2-[3-(p-fluorophenylthio)-propyl]-1,2,3,4-tetrahydro-γ-carboline hydrochloride A. p-fluorophenylthiopropionic acid To a solution of 10 g. of p-fluorothiophenol in 156 ml. of 1N aqueous sodium hydroxide is added 11.95 g. of β-bromopropionic acid, and the reaction stirred for 90 min. The reaction mixture is acidified to pH 4.0-5.0 with 6N hydrochloric acid and the reaction stored in the cold over a weekend. The resulting precipitate is filtered, washed with water and dried to give 13.8 g. (88% yield) of the intermediate, m.p. 67°-69° C.

B. 8-fluoro-5-(p-fluorophenyl)-2-(3-p-fluorophenylthiopripionyl)-1,2,3,4-tetrahydro-γ-carboline Dicyclohexylcarbodiimide (1.03 g.) is added portionwise to a stirred solution of p-fluorophenylthiopropionic acid (1.00 g.) in 10 ml. of methylene chloride cooled in an ice bath. After 15-20 min., a pale yellow precipitate forms. 8-Fluoro-5-(p-fluorophenyl)-1,2,3,4-tetrahydro-γ-carboline (1.42 g.) dissolved in 3 ml. of methylene chloride is added and the reaction mixture allowed to stir in the cold for 2 hrs. The reaction is allowed to warm to room temperature and stir overnight. The urea is filtered and the solvent removed in vacuo. The crude residual solid is dissolved in diethyl ethyl, the ether filtered, and the filtrate concentrated to dryness. The intermediate is isolated as a yellow solid, 1.8 g. (84% yield).

C. 8-Fluoro-5-(p-fluorophenyl)-2-[3-(p-fluorophenylthio)propyl]-1,2,3,4-tetrahydro-γ-carboline hydrochloride To a gently refluxing solution of 1.95 g. of 8-fluoro-5-(p-flurophenyl)-2-(3-p-fluorophenylthiopropionyl)-1,2,3,4-tetrahydro-γ-carboline in 25 ml. of dry tetrahydrofuran is added approximately 1.5 g. of lithium aluminum hydride in 25 ml. of tetrahydrofuran. After heating at reflux for 30 min., the reaction mixture is cooled in an ice bath and 250 ml. of water carefully added. The precipitate is filtered and washed on the filter with ethyl acetate. The aqueous filtrate is extracted several times with additional ethyl acetate which extracts were combined, washed with a brine solution, separated, and dried over sodium sulfate. Removal of the solvent gives the free base as a yellow oil, which when dissolved in ether treated with an ether solution of hydrogen chloride, provides the product hydrochloride, 1.5 g., m.p. 169°-171° C.

Mass Spectrum: Calc'd for $C_{26}H_{26}N_2F_3S\cdot HCL$ m/e: 452; Found: 452.

EXAMPLE 2

The procedures of Example 1 are repeated, starting with the appropriate γ-carboline and phenylthiopropionic acid, to give the following compounds:

8-fluoro-5-phenyl-2-[3-(p-chlorophenylthio)propyl]-1,2,3,4-tetrahydro-γ-carboline; 8-fluoro-5-phenyl-2-[3-(p-fluorophenylthio)propyl]-1,2,3,4-tetrahydro-γ-carboline; 8-fluoro-5-(p-chlorophenyl)-2-(3-phenylthiopropyl)-1,2,3,4-tetrahydro-γ-carboline; 8-fluoro-5-(p-chlorophenyl)-2-[3-(p-chlorophenylthio)propyl]-1,2,3,4-tetrahydro-γ-carboline; 8-fluoro-5-(p-methoxyphenyl)-2-[3-(p-methylphenyl)propyl]-1,2,3,4-tetrahydro-γ-carboline; 8-chloro-5-(p-fluorophenyl)-2-[3-(p-fluorophenylthio)propyl]-1,2,3,4-tetrahydro-γ-carboline; 8-chloro-5-(p-chlorophenyl)-2-[3-(p-chlorophenylthio)-propyl]-1,2,3,4-tetrahydro-γ-carboline; 8-chloro-5-phenyl-2-(3-phenylthiopropyl)-1,2,3,4-tetrahydro-γ-carboline; 8-chloro-5-(p-methoxyphenyl)-2-(3-phenylthiopropyl)-1,2,3,4-tetrahydro-γ-carboline; 8-chloro-5-(p-methoxyphenyl)-2-[3-(p-methylphenylthio)propyl]-1,2,3,4-tetrahydro-γ-carboline; 8-bromo-5-(p-chlorophenyl)-2-[3-(p-fluorophenylthio)propyl]-1,2,3,4-tetrahydro-γ-carboline; 8-bromo-5-phenyl-2-(3-phenylthiopropyl)-1,2,3,4-tetrahydro-γ-carboline; 8-bromo-5-(p-fluorophenyl)-2-[3-(p-methylphenylthio)propyl]-1,2,3,4-tetrahydro-γ-carboline; 8-bromo-5-(p-methoxyphenyl)-2-(3-phenylthiopropyl)-1,2,3,4-tetrahydro-γ-carboline; 8-bromo-5-(p-methoxyphenyl)-2-[3(p-chlorophenylthio)-propyl]-1,2,3,4-tetrahydro-γ-carboline; 5-phenyl-2-(3-phenylthiopropyl)-1,2,3,4-tetrahydro-γ-carboline; 5-(p-fluorophenyl)-2-[3-(p-fluorophenylthio)propyl]-1,2,3,4-tetrahydro-γ-carboline; 5-(p-chlorophenyl)-2-[3-(p-chlorophenylthio)propyl]-1,2,3,4-tetrahydro-γ-carboline; 5-phenyl-2-(3-phenylthiopropyl)-1,2,3,4-tetrahydro-γ-carboline; 5-(p-methoxyphenyl)-2-[3-(p-methylphenylthio)-propyl]-1,2,3,4-tetrahydro-γ-carboline; and 5-phenyl-2-[3-(p-fluorophenylthio)-propyl]-1,2,3,4-tetrahydro-γ-carboline.

EXAMPLE 3

8-Fluoro-5-(p-fluorophenyl)-2-(p-fluorophenylsulfinyl)-propyl]1,2,3,4-tetrahydro-γ-carboline hydrochloride A. p-fluorophenylsulfinylpropionic acid p-Fluorophenylthiopropionic acid (13.8 g.) is added with stirring to 152 ml. of 0.5M sodium meta periodate cooled to 0° C. To the resulting suspension is added 200 ml. of methanol and the reaction mixture allowed to stand overnight at refrigerator temperature. The solids are filtered and the methanol removed in vacuo from the filtrate. The precipitate is filtered, triturated with methylene chloride and filtered again to give 9.39 g. of the desired product, m.p. 143°–144° C.

B. 8-fluoro-5-(p-fluorophenyl)-2-[3-(p-fluorophenylsulfinyl)propionyl]-1,2,3,4-tetrahydro-γ-carboline To a suspension of 4.0 g. of p-fluorophenylsulfinylpropionic acid in 30 ml. of cold methylene chloride is added 3.18 g. of dicyclohexylcarbodiimide, and the reaction mixture stirred for 30 min. 8-Fluoro-5-(p-fluorophenyl)-1,2,3,4-tetrahydro-γ-carboline (5.25 g.) slurried in 15 ml. of methylene chloride is added and stirring continued in the cold for 2 hrs. The reaction mixture is allowed to warm to room temperature and remain at this temperature overnight. The suspension is cooled to 0° C. and the urea is filtered. The filtered precipitate is washed with methylene chloride and the washings and filtrate combined and concentrated to a foam. Trituration with n-hexane followed by drying of the solids gave 10.23 g. of crude product which is employed in the next step of the sequence without further precipitation.

C. 8-fluoro-5-(p-fluorophenyl)-2-[3-(p-fluorophenylsulfinyl)propyl]-1,2,3,4-tetrahydro-γ-carboline hydrochloride To a refluxing solution of 5.0 g. of 8-fluoro-5-(p-fluorophenyl)-2-[3-(p-fluorophenylsulfinyl)propionyl]-1,2,3,4-tetrahydro-γ-carboline in 30 ml. of dry tetrahydrofuran is added drop-wise a saturated lithium aluminum hydride in tetrahydrofuran solution until the excess foaming ceases. Refluxing is continued for an additional 30 min. and the reaction mixture subsequently cooled and carefully hydrolyzed with 250 ml. of water. The product is extracted from the resulting filtered precipitate and from the aqueous filtrate with ethyl acetate. The extracts are combined, washed with a brine solution and dried over magnesium sulfate. The solvent is removed in vacuo and the residue dissolved in diethyl ether. The addition of an ether solution saturated with hydrogen chloride results in the formation of 3.1 g. of the product as the hydrochloride salt, m.p. 160°–165° C.

EXAMPLE 4

The procedures of Example 3 are repeated, starting with the appropriately substituted γ-carboline and requisite phenylthiopropionic acid, to give the following congeners:

8-fluoro-5-phenyl-2-[3-(p-chlorophenylsulfinyl)-propyl]-1,2,3,4-tetrahydro-γ-carboline; 8-fluoro-5-phenyl-2-[3-(p-fluorophenylsulfinyl)propyl]-1,2,3,4-tetrahydro-γ-carboline; 8-fluoro-5-(p-chlorophenyl)-2-(3-phenylsulfinylpropyl)-1,2,3,4-tetrahydro-γ-carboline; 8-fluoro-5-(p-chlorophenyl)-2-[3-(p-chlorophenylsulfinyl)propyl]-1,2,3,4-tetrahydro-γ-carboline; 8-fluoro-5-(p-methoxyphenyl)-2-[3-(p-methylphenylsulfinyl)-propyl]-1,2,3,4-tetrahydro-γ-carboline; 8-chloro-5-(p-fluorophenyl)-2-[3-(p-fluorophenylsulfinyl)propyl]-1,2,3,4-tetrahydro-γ-carboline; 8-chloro-5-(p-chlorophenyl)-2-[3-(p-chlorophenylsulfinyl)propyl]-1,2,3,4-tetrahydro-γ-carboline; 8-chloro-5-phenyl-2-(3-phenylsulfinylpropyl)-1,2,3,4-tetrahydro-γ-carboline; 8-chloro-5-(p-methoxyphenyl)-2-(3-phenylsulfinylpropyl)-1,2,3,4-tetrahydro-γ-carboline; 8-chloro-5-(p-methoxyphenyl)-2-[3-(p-methylphenylsulfinyl)propyl]-1,2,3,4-tetrahydro-γ-carboline; 8-bromo-5-(p-chlorophenyl)-2-[3-(p-fluorophenylsulfinyl)propyl]-1,2,3,4-tetrahydro-γ-carboline; 8-bromo-5-phenyl-2-(3-phenylsulfinylpropyl)-1,2,3,4-tetrahydro-γ-carboline; 8-bromo-5-(p-fluorophenyl)-2-[3-(p-methylphenylsulfinyl)propyl]-1,2,3,4-tetrahydro-γ-carboline; 8-bromo-5-(p-methoxyphenyl)-2-(3-phenylsulfinylpropyl)-1,2,3,4-tetrahydro-γ-carboline; 8-bromo-5-(p-methoxyphenyl)-2-[3-(p-chlorophenylsulfinyl)-propyl]-1,2,3,4-tetrahydro-γ-carboline; 5-phenyl-2-(3-phenylsulfinylpropyl)-1,2,3,4-tetrahydro-γ-carboline; 5-(p-fluorophenyl)-2-[3-(p-fluorophenylsulfinyl)-propyl]-1,2,3,4-tetrahydro-γ-carboline; 5-(p-chlorophenyl)-2-[3-(p-chlorophenylsulfinyl)propyl]-1,2,3,4-tetrahydro-γ-carboline; 5-phenyl-2-(3-[p-methylphenylsulfinyl)propyl]-1,2,3,4-tetrahydro-γ-carboline; 5-(p-methoxyphenyl)-2-[3-(p-methylphenylsulfinyl)propyl]-1,2,3,4-tetrahydro-γ-carboline; and 5-phenyl-2-[3-(p-fluorophenylsulfinyl)-propyl]-1,2,3,4-tetrahydro-γ-carboline.

EXAMPLE 5

Test Procedures and Results

The effects of the compounds of the present invention on prominent amphetamine-induced symptoms were studied in rats by a rating scale modeled after the one reported by Quinton and Halliwell and by Weissman. Groups of five rats were placed in a covered plastic cage measuring approximately 26 × 42 × 16 cm. After a brief period of acclimation in the cage, the rats in each group were treated intraperitoneally (i.p.) with the test compound. They were then treated 1 hr. later with d-amphetamine sulfate, 5 mg./kg. i.p. One hour after amphetamine was given each rat was observed for the characteristic amphetamine behavior of moving around the cage. On the basis of dose-response data after amphetamine it was possible to determine the effective dose of the compound necessary to antagonize or block the characteristic amphetamine behavior of cage movement for fifty percent of the rats tested ($ED_{50}$). The time of rating chosen coincides with the peak action of amphetamine which is 60–80 min. after treatment with this agent.

Employing the above-described procedure, the following representative compounds were tested for their ability to block the behavior effects of amphetamine, the results being reported as the $ED_{50}$ in mg./kg. at the indicated times:

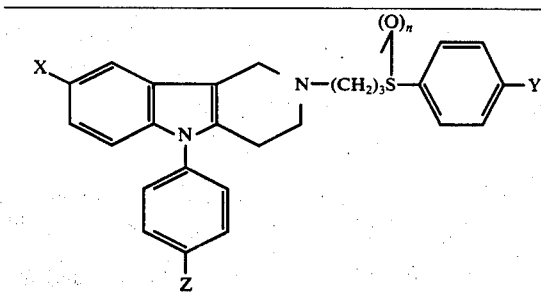

| X | Y | Z | n | $ED_{50}$; mg./kg. 1 hr. |
|---|---|---|---|---|
| F | F | F | 0 | 32 |
| F | F | F | 1 | 10 |

EXAMPLE 6

8-Chloro-5-(p-fluorophenyl)-2-[3-(p-fluorophenylsulfinyl)propyl]-1,2,3,4-tetrahydro-γ-carboline acetate Five grams of 8-chloro-5-(p-fluorophenyl)-2-[3-(p-fluorophenylsulfinyl)propyl]-1,2,3,4-tetrahydro-γ-carboline hydrochloride in 75 ml. of water is treated with 3 ml. of water containing 1.0 g. of sodium hydroxide, and the liberated free base extracted into 150 ml. of diethyl ether. The ether layer is separated, dried over magnesium sulfate and treated with 1 ml. of glacial acetic acid. The organic solvent and excess acetic acid are removed under reduced pressure and the residue triturated with hexane and filtered.

In a similar manner, other acid addition salts, especially those which are pharmaceutically acceptable, can be prepared.

EXAMPLE 7

Tablets

A tablet base is prepared by blending the following ingredients in the proportion by weight indicated:

| Sucrose, U.S.P. | 80.3 |
|---|---|
| Tapioca starch | 13.2 |
| Magnesium stearate | 6.5 |

Into this tablet base there is blended sufficient 8-fluoro-5-(p-fluorophenyl)-2-[3-(p-fluorophenylsulfinyl)propyl]-1,2,3,4-tetrahydro-γ-carboline hydrochloride to provide tablets containing 5.0 and 10 mg. of active ingredient per tablet. The compositions are each compressed into tablets, each weighing 360 mg., by conventional means.

EXAMPLE 8

Capsules

A blend is prepared containing the following ingredients:

| Calcium carbonate, U.S.P. | 17.6 |
|---|---|
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient 8-chloro-5-(p-fluorophenyl)-2-[3-(p-fluorophenylthio)propyl]-1,2,3,4-tetrahydro-γ-carboline hydrochloride to provide capsules containing 10, 15 and 20 mg. of active ingredient per capsule. The compositions are filled into conventional hard gelatin capsules in the amount of 350 mg. per capsule.

EXAMPLE 9

Suspension

A suspension of 8-fluoro-5-(p-fluorophenyl)-2-[3-(p-fluorophenylthio)propyl]-1,2,3,4-tetrahydro-γ-carboline sulfate is prepared with the following composition:

| Effective ingredient | g. | 25.00 |
|---|---|---|
| 70% aqueous sorbital | g. | 741.29 |
| Glycerine, U.S.P. | g. | 185.35 |
| Gum acacia (10% solution) | ml. | 100.00 |
| Polyvinylpyrrolidone | g. | 0.50 |
| Distilled water, sufficient to make 1 liter. | | |

To this suspension, various sweeteners and flavorants are added to improved the palatability of the suspension. The suspension contains approximately 25 mg. of effective agent per milliliter.

EXAMPLE 10

Sesame oil is sterilized by heating to 120° C. for 2 hrs. To this oil, a sufficient quantity of pulverized 8-fluoro-5-phenyl-[3-(p-fluorophenyl)propyl]-1,2,3,4-tetrahydro-γ-carboline hydrochloride to made a 0.025% suspension by weight. The solid is thoroughly dispersed in the oil by use of a colloid mill. It is then filtered through a 100–250 mesh screen and poured into sterile vials and sealed.

PREPARATION A

β-Carbolines

I.

8-Fluoro-5-(p-fluorophenyl)-1,2,3,4-tetrahydro-γ-carboline a. 8-fluoro-2-carbethoxy-1,2,3,4-tetrahydro-γ-carboline A mixture of 15.9 g. (0.093 mole) of N-carbethoxy-4-piperidone and 15.1 g. (0.093 mole) of p-fluorophenylhydrazine hydrochloride in 150 ml. of ethanol is heated to reflux for 2 hrs. The reddish reaction mixture is cooled and filtered, and the collected solids washed with a small amount of cold 95% ethanol, 21.3 g. (88% yield), m.p. 169°–170° C. The analytical sample is recrystallized from ethanol-water, m.p. 169°–170° C.

Anal. Calc'd for $C_{14}H_{15}O_2N_2F$: C, 64.1; H, 5.8; N, 10.7; Found: C, 63.8; H, 5.8; N, 10.6.

b. 8-fluoro-5-(p-fluorophenyl)-2-carbethoxy-1,2,3,4-tetrahydro-γ-carboline

To 30 ml. of N-methyl-2-pyrrolidione is added 3.45 g. (0.013 mole) of 8-fluoro-2-carbethoxy-1,2,3,4-tetrahydro-γ-carboline, 7.8 g. (0.045 mole) of p-fluorobromobenzene, 4.14 g. (0.014 mole) of cuprous bromide and 1.5 g. (0.014 mole) of sudium carbonate, and the resulting mixture heated in an oil bath at 200° C. for 6 hrs. The mixture is allowed to cool to room temperature overnight, and is then decanted into 300 ml. of water containing 60 ml. of ethylene diamine. Benzene (200 ml.) is added and the two-phase system is filtered through a super-cel pad. The filtrate is subsequently extracted several times with a total of 700 ml. of benzene. The extracts are combined, washed successively with water and a saturated brine solution and dried over anhydrous sodium sulfate. Removal of the solvent provides the crude product as a dark, residual oil.

The crude product in benzene is chromatographed on a silica gel column using 10% ethyl acetate-benzene as the elute. Fractions 1 through 16, comprised of 10–25 ml. each, and containing p-fluorobromobenzene, are collected and discarded. Fractions 16 to 38 are combined and concentrated in vacuo to an oil which solidifies on standing at 5° C. overnight. The product, 3.5 g. (76% yield), is triturated with pentane and filtered. The analytical sample is recrystallized from pentane, m.p. 118°–120° C.

Anal. Calc'd for $C_{20}H_{18}O_2N_2F_2$: C, 67.4; H, 5.1; N, 7.9. Found: C, 67.4; H, 5.2; N, 7.8.

c. 8-fluoro-5-(p-fluorophenyl)-1,2,3,4-tetrahydro-γ-carboline

A suspension of 3.56 g. (0.01 mole) of 8-fluoro-5-(p-fluorophenyl)2-carbethoxy-1,2,3,4-tetrahydro-γ-carboline and 8.2 g. (0.146 mole) of potassium hydroxide in 53 ml. of ethanol containing 5 ml. of water is heated to reflux overnight. An additional 3.0 g. of potassium hydroxide is added and the heating continued for 23 hrs. The brownish solution is cooled, concentrated in vacuo to dryness and partitioned between water and diethyl ether. The aqueous layer is further extracted with ether, and the ether layers combined, washed with a saturated brine solution and dried over magnesium sulfate. Removal of the solvent provides the desired product as an orange solid, 2.6 g. m.p. 125°–127° C. The analytical sample is recrystallized from pentane, m.p. 127°–128° C.

Anal. Calc'd for $C_{17}H_{14}N_2F_2$: C, 71.8; H, 5.0; N, 9.9. Found: C, 71.6; H, 5.1; N, 10.2.

The above mentioned procedure of Belgium Pat. No. 827,451 is employed, starting with the appropriate reagents, for the preparation of the intermediates, 1, leading to the compounds of the present invention.

What is claimed is:

1. A compound selected from those of the formula:

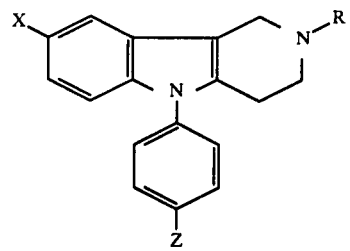

and the pharmaceutically acceptable acid addition salts thereof, wherein

X is selected from the group consisting of fluoro, chloro, bromo and hydrogen;

Z is selected from the group consisting of hydrogen, fluoro, chloro and methoxy; and R is

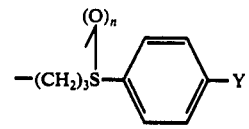

wherein $n$ is an integer of 0 or 1 and Y is selected from the group consisting of fluoro, chloro, methyl and hydrogen.

2. A compound of claim 1 wherein $n$ is 0 and Y is fluoro.

3. The compound of claim 2 wherein X is fluoro and Z is fluoro.

4. The compound of claim 2 wherein X is chloro and Z is fluoro.

5. The compound of claim 2 wherein X is fluoro and Z is hydrogen.

6. A compound of claim 1 wherein $n$ is 1 and Y is fluoro.

7. The compound of claim 6 wherein X is fluoro and Z is fluoro.

8. The compound of claim 6 wherein X is chloro and Z is fluoro.

9. The compound of claim 6 wherein X is fluoro and Z is hydrogen.

10. A method for tranquilizing a mammal displaying schizophrenic manifestations which comprises administering to said mammal in need of such treatment, a tranquilizing effective amount of a compound of claim 1.

11. A tranquilizing composition comprising an effective amount of a compound of claim 1 and a pharmaceutical acceptable carrier.

* * * * *